United States Patent
Malpensi et al.

(10) Patent No.: US 7,102,053 B2
(45) Date of Patent: Sep. 5, 2006

(54) METHOD FOR MAKING ABSORBENT ITEMS AND AN ABSORBENT ITEM OBTAINED USING THIS METHOD

(75) Inventors: Claudio Malpensi, Bologna (IT); Mario Gandini, Milan (IT)

(73) Assignee: GDM S.p.A., Bologna (IT)

(*) Notice: Subject to any disclaimer, the term of this patent is extended or adjusted under 35 U.S.C. 154(b) by 0 days.

(21) Appl. No.: 09/968,492

(22) Filed: Oct. 2, 2001

(65) Prior Publication Data

US 2002/0040209 A1 Apr. 4, 2002

(30) Foreign Application Priority Data

Oct. 2, 2000 (IT) .................... BO2000A0569

(51) Int. Cl.
*A61F 13/15* (2006.01)

(52) U.S. Cl. ............... 604/374; 604/367; 604/377

(58) Field of Classification Search ........... 604/385.01, 604/387, 385.17, 358, 374, 377, 367; 264/37.28; 156/94, 267
See application file for complete search history.

(56) References Cited

U.S. PATENT DOCUMENTS

| | | | | |
|---|---|---|---|---|
| 3,890,220 A | * | 6/1975 | Andedrson | 209/3 |
| 3,909,397 A | * | 9/1975 | Aldinger | 209/3 |
| 4,139,309 A | * | 2/1979 | Billingsley | 366/186 |
| 4,305,507 A | * | 12/1981 | Wittkopf | 209/3 |
| 4,902,559 A | * | 2/1990 | Eschwey et al. | 442/334 |
| 5,064,484 A | | 11/1991 | Craig et al. | |
| 5,190,533 A | * | 3/1993 | Blackburn | 604/367 |
| 5,573,523 A | * | 11/1996 | Whalen et al. | 604/374 |
| 5,730,737 A | | 3/1998 | Widlund et al. | |
| 5,817,394 A | * | 10/1998 | Alikhan et al. | 428/137 |
| 6,063,982 A | * | 5/2000 | Martin et al. | 604/374 |
| 6,410,819 B1 | * | 6/2002 | Vartiainen | 604/367 |

FOREIGN PATENT DOCUMENTS

| | | |
|---|---|---|
| FR | 2430734 | 2/1980 |
| GB | 2027593 | 2/1980 |
| JP | 11244330 | * 9/1999 |

* cited by examiner

*Primary Examiner*—John J. Calvert
*Assistant Examiner*—Jacqueline F Stephens
(74) *Attorney, Agent, or Firm*—Timothy J. Klima

(57) ABSTRACT

According to a method for making disposable diapers/adult incontinence pads, a diaper/incontinence pad is made whose pad is in three layers one on top of another; two outer layers of the pad consist of absorbent material and are positioned on opposite sides of an intermediate layer, which consists of a mixture of the absorbent material forming the two external layers and shredded material obtained by shredding faulty diapers/incontinence pads rejected from the diaper/incontinence pad production line.

24 Claims, 1 Drawing Sheet

METHOD FOR MAKING ABSORBENT ITEMS AND AN ABSORBENT ITEM OBTAINED USING THIS METHOD

BACKGROUND OF THE INVENTION

The present invention relates to a method for making absorbent items and an absorbent item obtained using this method.

The absorbent items according to the present invention are disposable items such as adult incontinence pads, diapers, ladies' sanitary towels and similar items. However, the following description refers, without limiting the scope of the invention, specifically to children's diapers/adult incontinence pads.

As is known, disposable diapers/incontinence pads comprise an absorbent pad which is normally within a soft retaining cover consisting of an inner permeable sheet of spun-bonded material and an impermeable polyethylene outer sheet, joined together and having shaped edges and elastic seals. The absorbent pad is normally made by feeding absorbent material, basically consisting of cellulose fiber, at the outer edge of a forming drum, whose outer edge has a plurality of suction seats shaped according to the desired anatomical shape for the pads. A forming drum of the above-mentioned type is known, for example, from U.S. Pat. No. 5,064,484.

Due to the complexity of both the diapers/incontinence pads themselves and the processes known for making them, diaper/incontinence pad production has a relatively high level of rejects. This, together with the high cost of the raw materials necessary for making the diapers/incontinence pads, results in significant economic losses.

SUMMARY OF THE INVENTION

The aim of the present invention is to provide a method for making absorbent items which allows the economic losses resulting from production rejects to be reduced or eliminated.

Accordingly, the present invention provides a method for making absorbent items, each of the absorbent items comprising a soft retaining cover, having a first and a second face which are opposite one another and consist of at least one sheet of material, and one pad, placed inside the cover between the first and second faces and obtained from at least one absorbent material. The method comprises steps of feeding the absorbent material to a pad forming device, and identifying and rejecting faulty absorbent items. The method comprises further steps of transferring the reject items to a shredder device, to obtain shredded material from the rejected items themselves; and feeding the shredded material to the forming device together with the absorbent material for making the pads.

Another aim of the present invention is to provide an absorbent item with low production costs.

Accordingly, the present invention provides an absorbent item of the type with a soft retaining cover, having a first and a second face which are opposite one another and consist of at least one sheet of material, and one pad, placed inside the cover between the first and second faces and obtained from at least one absorbent material. In addition to the customary absorbent material, the pad of the absorbent item comprises shredded material obtained by shredding the faulty items from a production line for said items.

BRIEF DESCRIPTION OF THE DRAWINGS

The present invention is now described with reference to the accompanying drawings, which illustrate a preferred embodiment of the invention without limiting its scope of application and in which.

DESCRIPTION OF THE PREFERRED EMBODIMENTS

With reference to the accompanying drawings, the numeral 1 denotes a production line for disposable diapers/adult incontinence pads 2.

Figure 2:
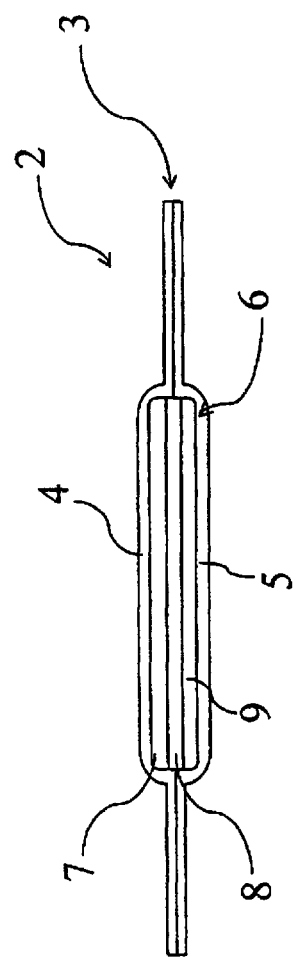
FIG. 2 is a cross-section of a preferred embodiment of the absorbent item in accordance with the present invention.

As illustrated in FIG. 2, each diaper/incontinence pad 2 comprises a soft retaining cover 3, which has a permeable face 4, consisting of a sheet of spun-bonded material and designed to make contact with the wearer's skin, and an impermeable face 5, consisting of a sheet of polyethylene, opposite the face 4 and stably connected to the face 4 in a known way, which is not illustrated.

The cover 3 is delimited by anatomically shaped edges, of the known type and not illustrated, along which there are elastic seals, also of the known type and not illustrated, and inside, between the faces 4 and 5, the cover holds a multi-layer pad 6 made using three layers 7, 8, 9 of absorbent padding, one on top of another.

The layers 7 and 9, respectively placed substantially in contact with the faces 4 and 5, comprise cellulose fiber mixed in a known way with particles of super-absorbent material, whilst the intermediate layer 8 comprises a mixture of cellulose fiber, particles of super-absorbent material and shredded material obtained by shredding faulty diapers/incontinence pads rejected from the production line 1. In particular, the cellulose fiber, the particles of super-absorbent material and the shredded material are present in a preset ratio in the above-mentioned mixture.

Figure 1:
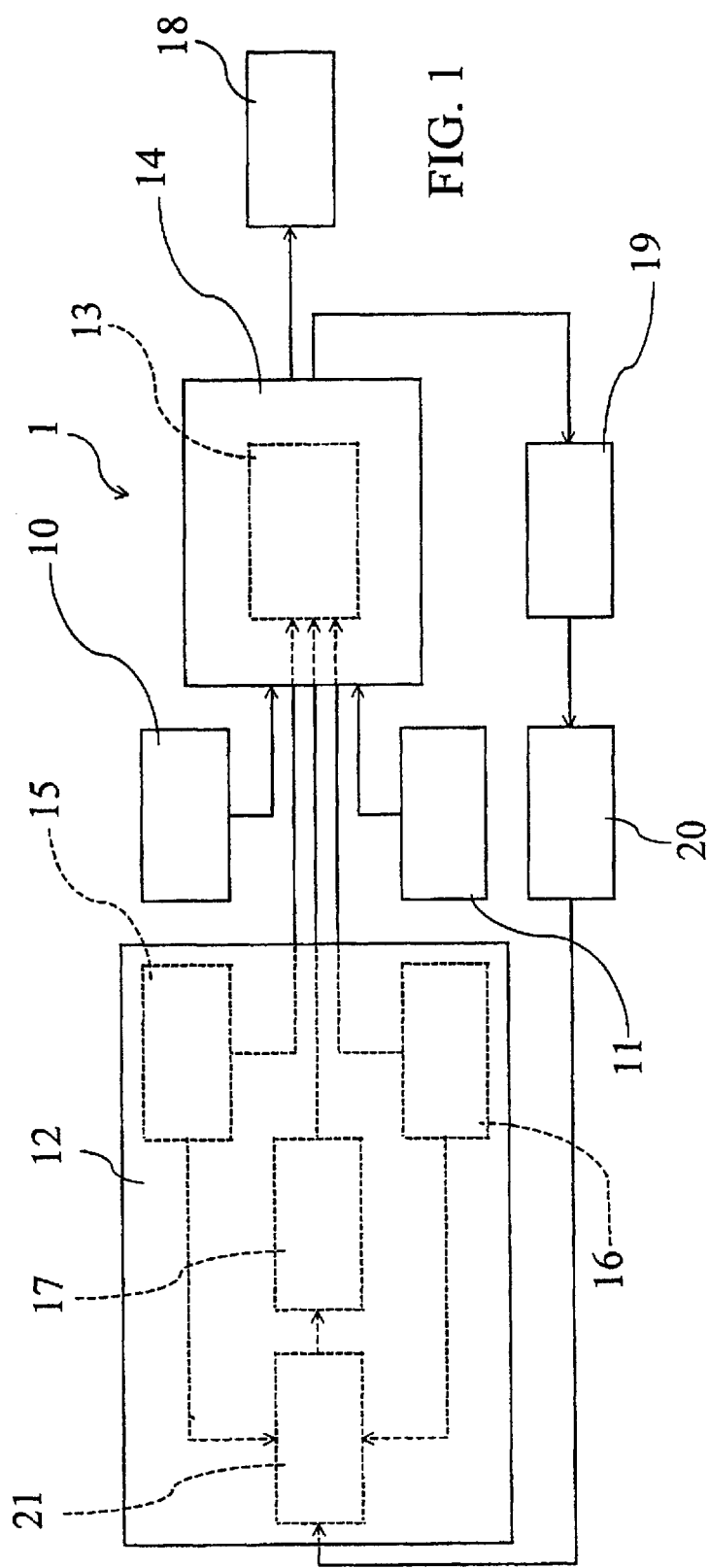
FIG. 1 is a block diagram of a system for implementing the method in accordance with the present invention.

The line 1 is now described with reference to the block diagram in FIG. 1, in which each block represents an operating unit of a known type, not requiring detailed descriptions.

The line 1 comprises a feed unit 10 for a web (not illustrated) of spun-bonded material for making the faces 4, a feed unit 11 for a web (not illustrated) of polyethylene for making the faces 5, and a feed unit 12 for the absorbent material for making the pads 6.

Specifically, the unit 12 is connected to a forming device 13 for the pads 6, which is part of a forming device 14 for the diapers/incontinence pads 2 and is of the known type for the formation of multi-layer pads.

The unit 12 comprises a feed device 15 for the cellulose fiber, a feed device 16 for the particles of super-absorbent material and a feed device 17 for the above-mentioned mixture of cellulose fiber, super-absorbent material and shredded material.

The device 14 for forming the diapers/incontinence pads 2 has an outfeed connected to a conveyor belt 18 for the diapers/incontinence pads 2 which are free of defects, and one or more collection points (not illustrated) for faulty diapers/incontinence pads connected to a conveyor belt 19, in turn connected to the infeed of a shredding mill 20.

The mill 20 outfeed is connected to the infeed of a mixer 21, which has another two infeeds, supplied respectively by the devices 15 and 16 and an outfeed connected to the feed device 17 for the mixture produced by the mixer 21.

Line 1 operation is easily deduced from the above and, therefore, does not require further explanation.

However, it should be emphasized how the diapers/incontinence pads 2 have, on the one hand, low production costs and, on the other hand, are as wearable and comfortable as conventional diapers/incontinence pads which do not contain the shredded and recycled material. In particular, the latter feature is guaranteed by the fact that the layer 8 containing the shredded material is placed between the two layers 7 and 9, in which the shredded material is completely absent.

The above is only one preferred embodiment of the method in accordance with the present invention. In simplified alternative embodiments, which are not illustrated, the device 13 can form pads consisting of a single layer in which free or controlled doses of the shredded material are mixed with the cellulose fiber and/or super-absorbent material, or it can form multi-layer pads with any given number n of layers, in which at least one layer comprises the shredded material, or, alternatively, consists exclusively of the shredded material.

What is claimed is:

1. An absorbent item of the type with a soft retaining cover, having a first and a second face which are opposite one another and comprising at least one sheet of material and one pad, the pad being inside the cover, between the first and second faces and comprising a first layer, the first layer comprising a mixture of a portion of at least one new absorbent material, and a portion of a shredded, recycled material derived from shredded faulty absorbent items from a production line for such items, the shredded, recycled material including a mixture of cellulose fiber, particles of super-absorbent material, permeable spun-bonded material and polyethylene.

2. The item according to claim 1, wherein the pad comprises at least two layers placed on top of one another; at least the first layer of the layers comprising the shredded material.

3. The item according to claim 2, wherein at least a second layer of the layers consists exclusively of the new absorbent material.

4. The item according to claim 1, wherein the absorbent material comprises at least one of cellulose fiber and super-absorbent particles.

5. The item according to claim 4, wherein the absorbent material comprises both cellulose fiber and super-absorbent particles.

6. The item according to claim 1, wherein the pad comprises at least three placed on top of one another; the first layer being positioned between a second and a third layer.

7. An absorbent item of the type with a soft retaining cover, having a first and a second face which are opposite one another and comprising at least one sheet of material and one pad, the pad being inside the cover, between the first and second faces and comprising at least one absorbent material; wherein, the pad of the absorbent item further comprising shredded, recycled material presenting a mixture of cellulose fiber, particles of super-absorbent material, permeable spun-bonded material and polyethylene obtained by shredding the faulty items made by a production line for said item, wherein the pad comprises at least three layers placed on top of one another; at least a first layer of the layers comprising the shredded material and being interposed between a second and a third layer.

8. The item according to claim 7, wherein at least one of the second and third layers consists exclusively of the absorbent material.

9. The item according to claim 1, wherein the first layer comprises a mixture, containing a given ratio of the shredded material and at least part of the absorbent material.

10. An absorbent item with a soft retaining cover, having a first and a second face which are opposite one another and comprising at least one sheet of material and one pad, the pad being inside the cover, between the first and second faces and comprising a first layer, the first layer comprising a mixture of a portion of at least one new absorbent material, and a portion of a shredded, recycled material.

11. The item according to claim 10, wherein the shredded material comprises shredded faulty absorbent pads.

12. The item according to claim 10, wherein the shredded material comprises shredded faulty absorbent items.

13. The item according to claim 10, wherein the pad comprises at least two layers of padding placed on top of one another.

14. The item according to claim 13, wherein at least a second layer of the layers consists exclusively of the new absorbent material.

15. The item according to claim 10, wherein the pad comprises at least three layers placed on top of one another; the first layer being interposed between a second and a third layer.

16. The item according to claim 15, wherein at least one of the second and third layers consists exclusively of the absorbent material.

17. The item according to claim 10, wherein the absorbent material comprises at least one of cellulose fiber and super-absorbent particles.

18. The item according to claim 17, wherein the absorbent material comprises both cellulose fiber and super-absorbent particles.

19. An absorbent item of the type with a soft retaining cover, having a first and a second face which are opposite one another and comprising at least one sheet of material and one pad, the pad being inside the cover, between the first and second faces and comprising at least one absorbent material; the pad further comprising shredded, recycled material, wherein the pad comprises at least three layers placed on top of one another; at least a first layer of the layers comprising to shredded material and being in an intermediate position between a second and a third layer.

20. An absorbent item comprising:
 a soft retaining cover;
 an absorbent pad positioned inside the cover, the absorbent pad comprising a first layer, the first layer comprising a mixture of a portion of new absorbent material and a portion of a shredded, recycled material.

21. The item according to claim 20, wherein the shredded material comprises shredded faulty absorbent pads.

22. The item according to claim 20, wherein the shredded material comprises shredded faulty absorbent items.

23. The item according to claim 22, wherein the shredded material comprises a mixture of cellulose fiber, particles of super-absorbent material, permeable spun-bonded material and polyethylene.

24. The item according to claim 23, wherein the absorbent item is one of a diaper and an incontinence pad.

* * * * *